United States Patent [19]

Hego et al.

[11] Patent Number: 5,770,021
[45] Date of Patent: Jun. 23, 1998

[54] PROCESS AND APPARATUS FOR PURIFICATION OF A GAS STREAM CONTAINING ACROLEIN

[75] Inventors: Michel Hego, Le Pont De Claix; Frédéric Kress, Vienne, both of France

[73] Assignee: Rhone-Poulenc Nutrition Animale, Antony Cedex, France

[21] Appl. No.: 675,487

[22] Filed: Jul. 1, 1996

[30] Foreign Application Priority Data

Jun. 29, 1995 [FR] France ................................. 95 07858

[51] Int. Cl.$^6$ ............................ B01D 3/00; B01D 59/00
[52] U.S. Cl. .................................. 203/8; 203/9; 203/49; 203/78; 203/84; 568/472
[58] Field of Search ........................... 203/8, 9, 49, 78, 203/84; 568/472

[56] References Cited

U.S. PATENT DOCUMENTS

| | | | |
|---|---|---|---|
| 3,433,840 | 3/1969 | Shima et al. ............................ 260/604 |
| 3,860,495 | 1/1975 | Borrel et al. ............................... 203/17 |
| 3,868,417 | 2/1975 | Dembgen et al. ......................... 203/49 |
| 3,926,744 | 12/1975 | Noll et al. ................................. 203/55 |
| 4,156,633 | 5/1979 | Horlenko et al. .......................... 203/93 |
| 4,199,410 | 4/1980 | Ohrui et al. ............................... 203/49 |
| 4,219,389 | 8/1980 | Biola et al. ............................... 568/41 |
| 4,225,516 | 9/1980 | Biola et al. ............................... 203/72 |
| 4,530,826 | 7/1985 | Ohashi et al. .......................... 423/376 |
| 5,326,916 | 7/1994 | Kobayashi et al. ..................... 568/492 |
| 5,352,837 | 10/1994 | Hsu et al. ................................. 568/41 |

FOREIGN PATENT DOCUMENTS

A-559227   9/1993   European Pat. Off. .

*Primary Examiner*—Nina Bhat
*Attorney, Agent, or Firm*—Finnegan, Henderson, Farabow, Garrett & Dunner, L.L.P.

[57] ABSTRACT

A process including a first stage wherein a feed gas stream containing acrolein originating, for example from the gas-phase oxidation of propylene to acrolein, is fractionated into a gaseous effluent and a liquid stream in a cooling column operating such that the temperature of the liquid stream at the bottom of the column is lower than or equal to the condensation temperature of the feed gas stream, the difference in temperature not exceeding 20° C. and, a second stage, wherein the gaseous effluent is condensed at a temperature that is lower than 20° C., to give a liquid fraction and a purified gaseous fraction, is disclosed. An apparatus for carrying on the purification process is also disclosed.

28 Claims, 3 Drawing Sheets

PROCESS AND APPARATUS FOR PURIFICATION OF A GAS STREAM CONTAINING ACROLEIN

The present invention is directed to a process for the purification of a gas stream containing acrolein to extract the acrolein therefrom. A major industrial use of acrolein, which is a raw material, is the synthesis of beta-methylthiopropionaldehyde (MTPA) by reaction of acrolein with methyl mercaptan.

Acrolein is produced by gas-phase oxidation with air in the presence of water. This gas-phase oxidation conventionally produces a gaseous mixture comprising acrolein in an amount that is greater than 10% by weight, gases such as nitrogen, oxygen, carbon monoxide, and carbon dioxide, propylene, water and reaction by-products such as acrylic acid, acetic acid and formic acid, formaldehyde, acetaldehyde, allyl alcohol and polymers resulting from the degradation of acrolein and of acrylic acid in particular. With a view towards using the acrolein in subsequent reactions, such as the direct synthesis of MTPA, the water, the acidic impurities, especially acrylic acid, and the heavy polymer reaction by-products must be at least partly separated from the complex gaseous mixture that is produced.

Direct synthesis of MTPA is described in patents U.S. Pat. No. 4,225,516 and U.S. Pat. No. 5,352,837, for example. The synthesis of MTPA includes reacting a purified gaseous mixture containing acrolein with a source of methyl mercaptan in a solution of methylthiopropionaldehyde. The limits of water and of acids, particularly acrylic acid, in the purified gaseous mixture that can be employed are very important because they determine the performance of the reaction.

A number of methods for purifying acrolein are known and have been exploited. A first method, according to U.S. Pat. No. 4,219,389, incorporated herein by reference, includes extracting acids present in the gaseous mixture containing acrolein by absorption in an organic solvent, in particular, 2-ethylhexanol or tributyl phosphate. However, this type of method has the disadvantage that the solvent which is used must be purified before being recycled into the process, increasing the cost of the process.

A second method of purifying acrolein, for example, according to U.S. Pat. No. 3,433,840, incorporated herein by reference, includes extracting acids present in the gaseous mixture containing acrolein by selective absorption with water and then recovering the acrolein present in the gaseous stream laden with water and non-condensables originating from the absorption stage by distilling the resulting liquid mixture to obtain an acrolein/water azeotrope. However, this type of process has the disadvantage of requiring large quantities of water for the absorption step. This process also presents considerable risks of degradation of the acrolein and its polymerization during the distillation stage.

Another route has been developed with a view to the direct synthesis of MTPA. The gaseous mixture produced by the oxidation of propylene is first purified to remove as many of the acidic compounds as possible by absorption with water. After condensation of the water, acrolein is extracted from the residual gas by absorption in cold MTPA originating from an MTPA production reactor. The solution of acrolein in MTPA that is obtained is then introduced directly into the MTPA production reactor with methyl mercaptan. Such a process is described, for example, in U.S. Pat. No. 4,225,516, incorporated herein by reference. However, since preliminary purification of the starting mixture containing acrolein to remove the acids is still required, the disadvantages mentioned earlier are still encountered.

Another known process for purification of acrolein is described in European Patent Application No. EP-A-0,559,227, incorporated herein by reference. This process includes cooling the reaction mixture in a cooling tower, where it is brought into contact with condensed liquid, an effluent gas containing predominantly non-condensables and acrolein being recovered at the top of the tower. Under the conditions described, where the condensate at the bottom of the tower is at a temperature of 35° to 50° C., the effluent gas at the top of the tower is at a temperature of 35° to 55° C., and where the residence time of the condensate in the tower is short, purification of the reaction mixture results in absorption of a relatively large quantity of acrolein in the condensate, corresponding to a content of approximately 3% by weight.

The present invention seeks to overcome the disadvantages of the known processes and to provide a process for the purification of acrolein from a gaseous mixture of acrolein, water, acids and non-condensables, and thus to permit the direct use of acrolein, in particular in the synthesis of MTPA.

It is also an object of the present invention to produce acrolein such that the purification yield is as high as possible while reducing to a minimum the risk of degradation of the acrolein. Finally, an aim of the present invention is to avoid the fouling of equipment used in the process.

Accordingly, the present invention provides a process for the purification of acrolein present in a feed gas stream including acrolein, water, acids and inert gases, originating particularly from the gas-phase oxidation of propylene to acrolein, which process comprises, in a first stage, fractionating the feed gas stream into a gaseous effluent and a liquid stream in a cooling column operating such that the temperature of the liquid stream at the bottom of the column is lower than or equal to the condensation temperature of the feed gas stream, the difference in temperature not exceeding 20° C., preferably not exceeding 10° C.; and then, in a second stage, condensing the gaseous effluent at a temperature that is lower than 20° C. to give a liquid fraction and a purified gaseous fraction.

The acids present in the feed gas stream are generally organic acids, usually acrylic acid, formic acid, acetic acid and maleic acid. As used herein, the term "inert gases" is intended to mean all of the gaseous compounds that remain in the gaseous phase from the beginning to the end of the production process of the invention and that are found in the purified gaseous fraction after the condensation stage. In this respect, the inert gases in the mixture to be purified may, in what follows, be occasionally called "non-condensables" since they are not condensed under the temperature and pressure conditions used in the process of the invention. The inert gases generally include nitrogen, oxygen and other gases from air, carbon oxides and propylene.

By virtue of the process of the invention it is possible, at the end of the second stage, to obtain a purified gaseous fraction containing acrolein and non-condensables, in which the weight content of water is lower than or equal to 2% and the weight content of acids is lower than or equal to 100 ppm.

In the first stage of the process of the invention, the feed gas stream that typically originates from the gas-phase oxidation of propylene is preferably cooled from its production temperature to a temperature ranging from 100° to 200° C. and is introduced into the bottom part of the cooling column.

The feed stream of the cooling column preferably contains from 10 to 15% by weight of acrolein and approximately from 20 to 30% by weight of water and less than 5% by weight of acrylic acid, more preferably, less than 2% by weight. The remainder consisting of non-condensable gases and of various organic constituents produced in the oxidation of propylene.

The circulation of the gaseous stream in the column countercurrentwise to a cold liquid results in condensation of the water and acrylic acid and of the other condensable components that may be present. The condensed liquid flows back down under gravity to the bottom of the column. The gases at the top of the column are depleted in impurities and include acrolein and non-condensable gases. The temperature of the gases at the top of the column preferably ranges from 30 to 60° C., and still more preferably ranges from 50° to 60° C.

The temperature of the liquid stream at the bottom of the column is preferably less than 20° C., and more preferably less than 10° C., lower than the condensation temperature of the feed gas stream. Preferably, the temperature of the liquid stream at the bottom of the column is substantially equal to the condensation temperature of the gaseous mixture introduced into the column to reduce to a minimum condensation of the acrolein and its degradation; in most cases it is lower than 100° C. The condensation temperature of the gaseous mixture originating from the catalytic oxidation of propylene and containing approximately from 10 to 15% by weight of acrolein and from 20 to 30% by weight of water preferably ranges from 70° to 90° C., at a pressure of approximately $1.2 \times 10^5$ Pa.

The cooling column preferably operates at a pressure ranging from $10^5$ to $3 \times 10^5$ Pa.

The residence time of acrolein in the cooling column preferably ranges from 5 to 10 minutes. At this residence time, the risk of degradation is limited while the impurities are removed efficiently using the process of the invention.

According to the process of the invention, a portion of the liquid stream accumulated in the bottom of the cooling column is preferably removed, optionally cooled, and recycled as circulating cold liquid stream in the cooling column. A compound that inhibits the polymerization of acrolein and of acrylic acid may be added to the recycled liquid stream. The polymerization inhibitor is preferably chosen from hydroquinone, phenothiazine, and derivatives of phenothiazine.

The recycled stream generally contains organic acids, including acrylic acid, and preferably less than 2%, more preferably less than 1.5%, by weight of acrolein and at least 90% by weight of water.

The recycled liquid stream may be introduced into the cooling column in one or more places. It is preferably injected at the top of the column to spray the gaseous mixture to be treated. More preferably, the recycled liquid is cooled to a temperature ranging from 15° to 45° C. by a cooler using industrial water or a cooler using water containing glycol.

According to an optional stage of the process of the invention, another portion of the liquid stream accumulated at the bottom of the cooling column is preferably removed to undergo a stripping operation to recycle to the bottom of the column a portion of the acrolein entrained in gaseous form. The liquid stream removed for this purpose is preferably heated to a temperature ranging from 90° to 120° C. before the stripping.

The stripping operation is carried out by circulating the liquid stream removed to a column, countercurrentwise to an inert gas, preferably nitrogen, the liquid being introduced at the top of the column and the gas being introduced into the bottom part of the column. The temperature of the stripping gas preferably ranges from 130° to 160° C., more preferably is approximately 150° C., in order to eliminate any risk of degradation of the acrolein and to improve stripping efficiency.

During the operation acrolein present in the liquid stream is extracted by the stripping gas, with the result that a gaseous stream is recovered containing acrolein, a small portion of water and non-condensables. Most of the acids and water remain in the liquid phase.

The pressure in the stripping column is preferably higher than the pressure in the cooling column to allow the gaseous stream produced by stripping to be reinjected into the cooling column with the feed gas stream. It should be noted that the pressure in the stripping column must not be too high otherwise stripping efficiency is impaired. One skilled in the art will be able to determine the appropriate pressure to use to avoid impairment of the stripping efficiency.

Return of the gaseous stream produced by the stripping operation may be carried out by mixing the stripped stream with the feed gas stream or, preferably, by injection of the stripped stream into the cooling column, approximately at the same height as the feed gas stream entry.

In the second stage of the process according to the invention, the gas leaving the top of the cooling column is partly condensed, preferably in a surface condenser. Separation of the condensed liquid phase provides a gas that is depleted in impurities, especially in water and in acids, and containing acrolein and non-condensables.

The gaseous effluent is preferably condensed once, or several times in succession, to give a gaseous fraction containing acrolein, the temperature of the gas leaving the last condenser being lower than 20° C. Condensation of the gaseous effluent is preferably carried out in the presence of an acrolein polymerization inhibitor.

At the end of the condensation operation(s) the gaseous fraction containing acrolein may be recovered as purified gas, which may be used directly in the synthesis of MTPA.

According to an additional optional stage, the gaseous fraction may preferably be subjected to an absorption operation by circulation countercurrentwise to water, to further remove additional residual acids. This operation may be carried out in an absorption column. The water circulates countercurrentwise to the gaseous fraction at a temperature that is lower than the temperature of the fraction, with a mass flow rate such that the ratio of the mass flow rate of water to the mass flow rate of the gaseous fraction preferably ranges from 0.005:1 to 0.051, and more preferably from 0.01:1 to 0.05:1. A purified gas is thus obtained in which the water content is preferably lower than 2% by weight, and more preferably lower than or equal to 1% by weight, and the acid content is preferably lower than 100 ppm.

The ratio ranges of water mass flow rate to the mass flow rate of the gaseous fraction are expressed for an absorption performed in a column preferably comprising from 5 to 10 theoretical plates. The use of a column that has a number of plates outside the values referred to is possible. In this case, a person skilled in the art is capable of adapting the water and gaseous fraction flow rates accordingly.

Also, in order to increase the efficiency of absorption in water, and hence to conform to the desired water and acid contents in the purified gas, it is preferred that the gas should be as cold as possible. Consequently, it is preferred to supercool the gas in the condensation operation.

A compound of the type described above which inhibits the polymerization of acrolein is preferably added to the water for absorption. However, during the absorption operation, dissolving chemical species in the water has the effect of reheating the gas leaving the absorption column.

A water content in the purified acrolein-containing gas of lower than 2% by weight, and a total acid content of lower than 100 ppm, are values that are preferred for the use of the gas as starting material for the direct synthesis of MTPA.

Another embodiment of the present invention is an apparatus intended for implementing the process of the invention as described above. This apparatus includes a cooling column supplied with a feed gas stream by means for feeding gas, a condensation unit provided with means for feeding gas from the top of the cooling column and, optionally, a stripping column fed at the top by means for feeding liquid from the bottom of the cooling column and means for recirculating the gas from the top of the stripping column to the means for feeding gas or to the lower part of the cooling column.

The plant preferably additionally includes means for circulating liquid from the bottom of the cooling column to one or more points of the upper part of the cooling column, after the liquid has been cooled by means of a heat exchanger.

When the apparatus includes a stripping column, a preheater is preferably installed upstream of the column to raise the temperature of the liquid to be stripped.

An example of an embodiment of the invention will now be described with reference to FIGS. 1, 2 and 3 of the attached drawings, which show, respectively, three embodiments of an apparatus in accordance with the invention for purification of a gaseous stream containing acrolein.

Figure 1:
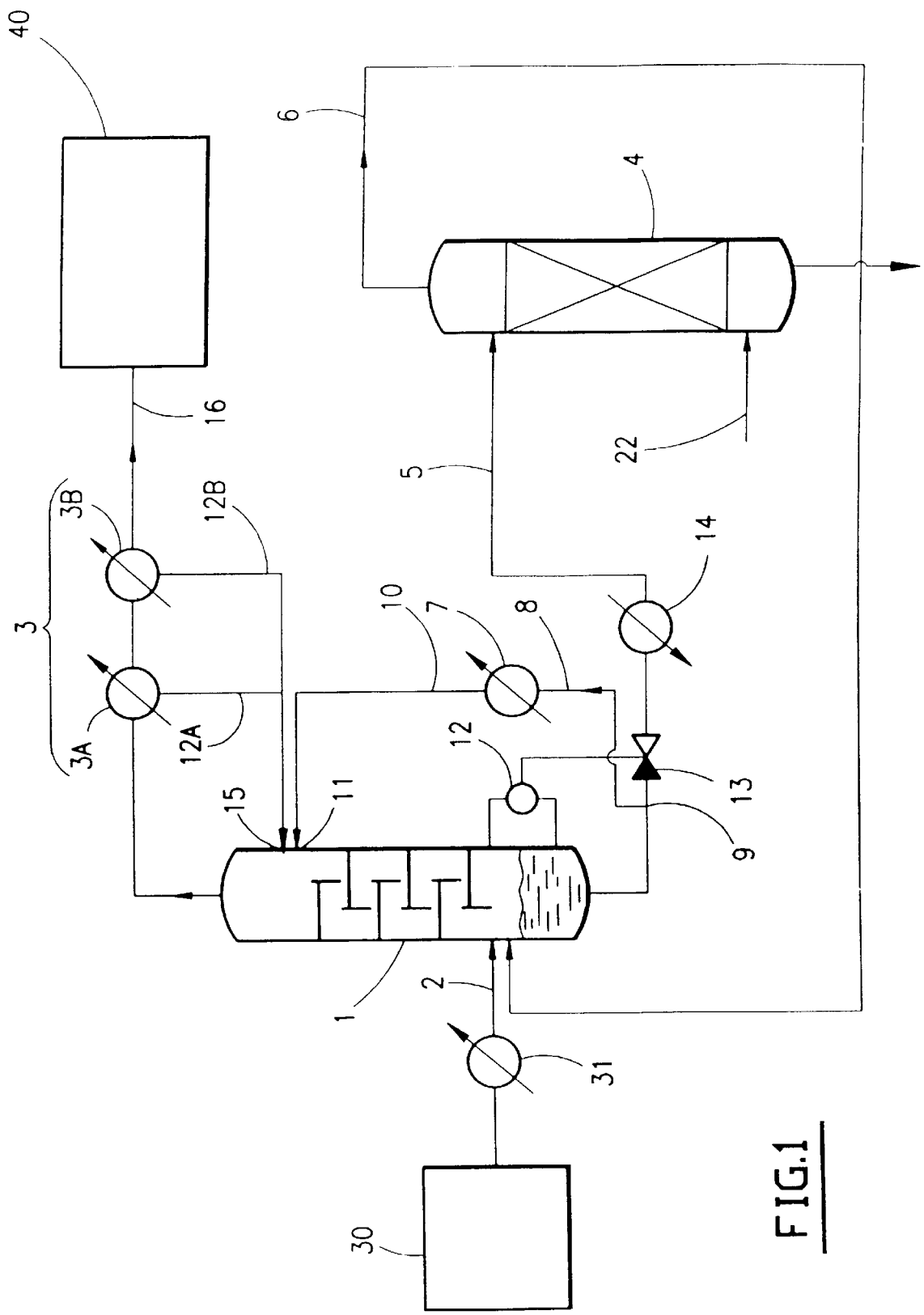
FIG. 1 depicts a purification apparatus for gas-phase oxidation of propylene and for producing a gaseous stream containing purified acrolein which feeds an MTPA synthesis unit.

The apparatus shown in FIG. 1 is intended for the purification of a gaseous mixture originating from a unit 30 for the gas-phase oxidation of propylene and for producing a gaseous stream containing purified acrolein which feeds an MTPA synthesis unit 40. The apparatus of FIG. 1 comprises a cooling column 1, a condensation unit 3 made up of two separate condensers 3A and 3B, a cooler 7, a heater 14, and a stripping column 4, the top of which is connected via a gas delivery conduit 6 to the bottom part of the cooling column 1.

The apparatus operates in the following manner.

The feed gas stream produced at unit 30 is first cooled to a temperature, for FICES example, ranging from 100° to 200° C. in heat exchanger 31.

The cooled feed gas is then introduced, via a feed conduit 2, into the lower part of the cooling column 1. The cooling column 1 may be a cooling column of any known type, for example a packed column; it being possible for the packing to be chicanes or trays.

Feeding with the gaseous stream to be purified is preferably performed in the lower quarter of the cooling column, whereas a fraction of the condensed liquid is introduced at the top of the column. The cooling column advantageously operates at a pressure ranging from $10^5$ to $3 \times 10^5$ Pa.

The cooling of the gas in column 1 produces, at the top of the column, gases whose temperature preferably ranges from 30° to 60° C., and more preferably ranges from 50° to 60° C., while a liquid stream whose temperature corresponds to the condensation temperature of the feed gas stream accumulates at the bottom of the column.

The sizing of the cooling column is carried out according to the knowledge of a person skilled in the art as a function of these operating parameters. The height thus depends on the heat load to be removed and the difference in temperature between the condensed liquid fed at the top of the column and the liquid stream deposited at the bottom and the diameter and on the speed of the gases in the column.

The gases from the top of the cooling column are conveyed towards the condensation unit 3, which, in the embodiment shown in FIG. 1, comprises two separate condensers, 3A and 3B, in series. In fact, the condensation unit 3 may be made up of a variable number of condensers; a single condenser may even be sufficient. In general, the choice of the number of condensers depends on the difference in temperature between the gases from the top of the cooling column and the gas that feeds the MTPA synthesis unit, and on the area of the heat exchange units. A surface condenser, or condensers, is/are preferably employed.

Gas cooled in the condenser 3A and separated off on leaving the latter, depleted in impurities such as water and acrylic acid, is conveyed towards the entry of the condenser 3B, while the condensed liquid containing water and particularly acrylic acid, separated off on leaving the condenser 3A, is removed via a conduit 12A. On leaving the condenser 3B, gas separated off, further depleted in impurities such as water and acrylic acid, is conveyed in a conduit 16 towards the MTPA unit 40, while the liquid condensed in 3B, containing water and particularly acrylic acid, is removed via a conduit 12B.

To cool the gases from the top of the cooling column from their column top temperature (preferably 30° to 60° C., more preferably 50° C. to 60° C.) to a temperature that is lower than 20° C., it is preferable that the condenser 3A should operate with a conventional cooling liquid such as industrial water, and that the condenser 3B should operate with a more complex cooling liquid such as brine (water and calcium chloride) or else water containing glycol.

Although polymerization of acrolein is not very fast at the low temperature of the condensers, it is preferable to reduce the residence time of acrolein in the condensers to a minimum. To this end, it is advantageous to employ vertical tubular condensers.

According to an alternative embodiment, not shown in FIG. 1, the condensers 3A and 3B may be equipped with means for introducing a compound which inhibits the polymerization of acrolein, such as hydroquinone.

In the embodiment shown in FIG. 1, the conduits 12A and 12B removing the liquids produced during the condensation are connected to the upper part of the cooling column 1, at a point 15, in order to introduce condensed liquid, typically containing water and acrylic acid. The point 15 is preferably situated in the upper quarter of the column. Circulation of the condensed liquid towards the bottom of the cooling column 1, in intimate contact with the gaseous stream rising in the column, provides some of the cooling of the latter.

The liquid stream accumulated at the bottom of the cooling column I contains impurities such as water, acrylic acid and heavy condensables, but also contains a portion of acrolein from the feed gas stream. Some condensed liquid is therefore removed from the bottom of the cooling column 1 in a liquid delivery conduit 5, connected to the top of the stripping column 4.

In the embodiment shown in FIG. 1, a portion of this condensed liquid stream is removed at a point 9 of the conduit 5, via an abstraction conduit 8. This conduit feeds the entry of a cooler 7 to cool the bottom liquid from its initial temperature to a temperature ranging from 15° to 45° C. The liquid cooled in cooler 7 is reinjected into the cooling column 1 via a conduit 10 at a point 11. Point 11 is preferably situated in the upper part of the column 1, preferably in the upper quarter. Point 11 is advantageously close to the above-mentioned point 15. The cooler 7 may be chosen from any of the known types of heat exchangers.

The other portion of the liquid stream removed at the bottom of the column 1 is conveyed via the conduit 5 to the stripping column 4. The stripping column is a packed column of any known type; a column containing packing or a column containing trays may be employed. The conduit 5 injects the liquid to be stripped into the upper part of the stripping column 4. An "inert gas", such as nitrogen, injected into the lower part of the stripping column 4 via the conduit 22 is employed as stripping gas. This gas is preferably preheated to a temperature ranging from 130° to 160° C., more preferably to approximately 150° C., to improve the stripping efficiency.

In the embodiment shown in FIG. 1, a heat exchanger 14 is installed at an intermediate point of the conduit 5 upstream of the column 4 and downstream of the point 9. This exchanger functions as a heater to raise the temperature of the liquid mixture to be stripped to a value of the order ranging from 90 to 120° C., with the aim of improving the efficiency of the stripping stage.

The inert stripping gas desorbs acrolein from the liquid mixture as it rises in the stripping column 4, with the result that a gaseous fraction containing water, non-condensables and acrolein is recovered at the top of this column. This gaseous fraction is reinjected into the lower part of the cooling column 1, via the gas delivery conduit 6, preferably into the bottom quarter of the cooling column 1. The injection of gas via the conduit 6 is preferably performed at the same height as the injection of the feed gas stream via the conduit 2.

In an alternative embodiment, the conduit 6 may be connected to the conduit 2 upstream of the entry of the cooling column 1, in order to mix the gaseous fraction produced by the stripping with the gaseous stream to be purified.

To permit the gases recovered at the top of the stripping column 4 to return into the cooling column 1, the pressure in the stripping column 4 is advantageously kept higher than the pressure prevailing in the cooling column 1. The pressure in the stripping column 4 is preferably slightly higher than the pressure prevailing in the cooling column 1.

The cooling column 1 is endowed with a system for drawing off liquid from the bottom of the column, intended to keep the level of liquid constant at the bottom of the column. Any known means for drawing off liquid may be employed, particularly means 12 for controlling the liquid level at the bottom of the cooling column 1 and a valve 13 as shown in FIG. 1. Opening of the valve 13 enables the surplus of liquid accumulated at the bottom to be removed via the conduit 5, towards the stripping column 4 or the cooler 7.

Figure 2:
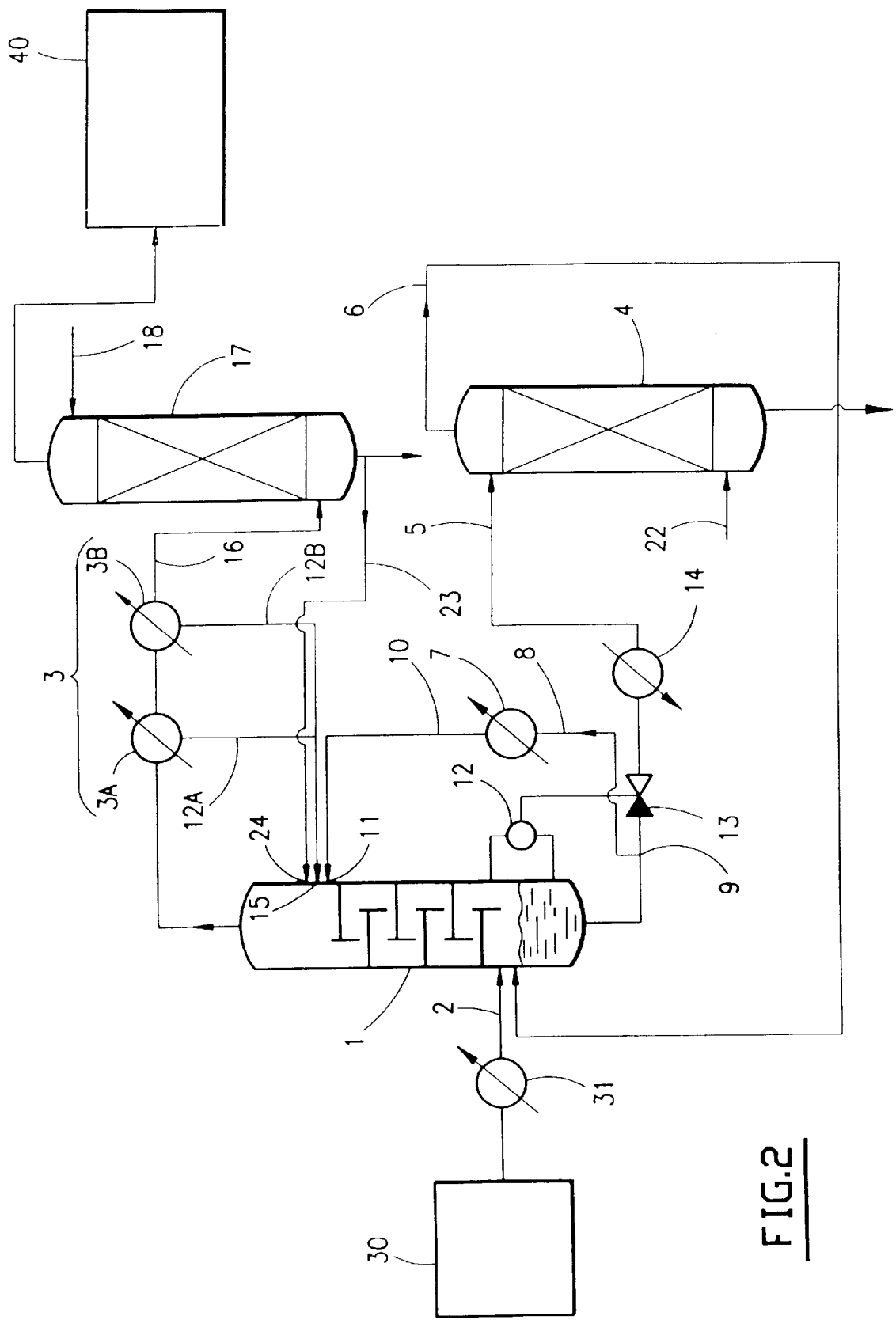
FIG. 2 is an alternative embodiment of FIG. 1 wherein the gas delivery conduit is connected to a liquid/gas absorption column.

The apparatus shown in FIG. 2 is an alternative embodiment of the apparatus shown in FIG. 1, from which it differs in the following ways.

The gas delivery conduit 16 is connected to a liquid/gas absorption column 17. This column is a packed column which may be of any known type, preferably a column containing packing or a column containing trays.

Conduit 16 allows gas depleted in impurities, originating from the condensation unit 3, to be injected into the lower part of the column 17, while the latter is fed in its upper part via a water delivery conduit 18. The water travelling countercurrentwise absorbs the last traces of acid, usually acrylic acid. This water, which is collected at the bottom of the column 17, may be reinjected into the upper part of the cooling column 1, as cooling liquid. This water, laden with traces of acid, is preferably conveyed via the conduit for removing liquid 23 towards a point 24 of the cooling column 1, advantageously situated above the point 15. The temperature of the water introduced into the column 17 is advantageously lower than 20° C.

Water delivered by the conduit 18 preferably contains a compound which inhibits the polymerization of acrolein. The compound is preferably added to the water upstream of the absorption column 17.

Figure 3:
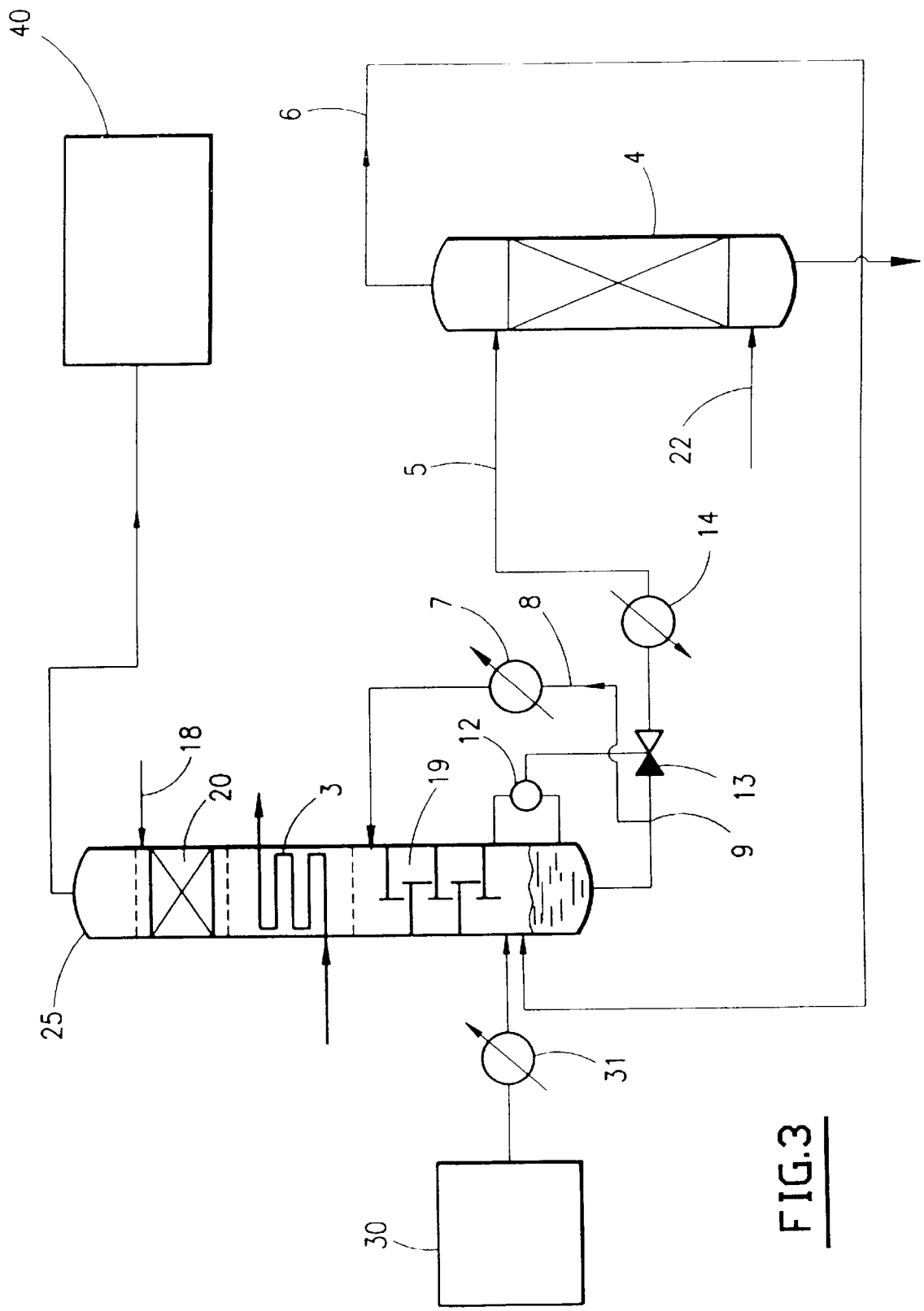
FIG. 3 is an alternative embodiment of FIG. 2 wherein the apparatus includes a column which encloses a cooling column in its lower part, a condensation unit in its intermediate part and an absorption column in its upper part.

The apparatus shown in FIG. 3 is an alternative embodiment of the apparatus shown in FIG. 2, in which the layout of the units is slightly different.

Thus, the apparatus includes a column 25 enclosing a cooling column 19 in its lower part, a condensation unit 3 in its intermediate part and an absorption column 20 in its upper part.

The cooling column 19 is a cooling column that is identical to the cooling column 1, the top of which is in direct communication with the entry of the condensation unit 3. The gaseous effluent resulting from the fractionation in the cooling column 19 is thus conveyed directly into the condensation unit 3, which may be made up of one or more condensers in series. The liquid condensed in the condensation unit 3 travels freely, descending into the lower part of the column 25, countercurrentwise to the feed gas stream, and accumulates in the bottom with the liquid stream condensed in the cooling column.

The gaseous fraction depleted in impurities leaving the condensation unit 3 enters directly into the upper part of the column 25, where the absorption column 20 is placed. The absorption column 20 is similar in type to the absorption column 17, except that the injection of the gas no longer takes place via a gas delivery conduit.

The upper part of the absorption column 20 is fed with water via a water delivery conduit 18 connected to the upper part of the unit 25.

The water travels countercurrentwise to the gas rising in the absorption column and picks up the residual acidic impurities present in this gas. It then flows freely back down in the intermediate part and the lower part of the column 25 and accumulates at the bottom with the other liquid fractions.

The column 25 is advantageously endowed with means enabling a back-pressure to be created between the cooling column 19 and the upper section. A hydraulic ram may be installed for this purpose.

Each of the apparatuses described above makes it possible to perform the purification of a mixture containing acrolein, water and acids such as acrylic acid, to supply a gaseous stream containing purified acrolein. Preferably, a purified gas is thus produced which has a water content lower than 2% by weight and a total acid content lower than 100 ppm, without fouling the equipment and while limiting the degradation of acrolein.

The following examples illustrate the present invention.

EXAMPLE 1

An apparatus of the type shown in FIG. 1, including a condenser as condensation unit, was employed for purifying a gaseous mixture originating from a reactor for vapour-phase oxidation of propylene to acrolein. The composition of the mixture was as follows.

(The portions are shown in relation to the weight of the mixture.)

| | |
|---|---|
| Non-condensable gases (nitrogen, oxygen, propylene, carbon oxides) | 63.3% |
| Water | 21.0% |
| Acrolein | 12.3% |
| Acrylic acid | 1.4% |
| Other (acetaldehyde, allyl alcohol, formaldehyde etc.) | 2.0% |

The gaseous mixture to be purified was introduced at a temperature of 180° C. at the bottom of a cooling column having 10 perforated trays below the final tray, at a mass flow rate of 20 kg/h, and at a pressure of $1.2 \times 10^5$ Pa.

The liquid at the bottom of the column was maintained at a temperature of 70.3° C., while the condensation temperature of the feed gas stream was 74.7° C. (the difference being equal to 4.4° C.). The feed gas contained 1.3% by weight of acrolein.

The recycling of liquid from the bottom to the top of the column took place at a flow rate of 80 kg/h, the heat exchanger supplied a recycled liquid at a temperature of 30° C.

Another portion of the liquid from the bottom of the column was conveyed into the nitrogen stripping column, which was filled with random bulk packing, and which operated at a temperature of 90° C. with a stripping nitrogen mass flow rate of 0.6 kg/h. A liquid containing not more than 100 ppm of acrolein was recovered from it.

At the exit of the cooling column the top gases were cooled to 2° C. in the condenser. The gaseous fraction recovered at the exit of the condenser was analyzed to determine its acid and water contents.

The determination of the content of the organic acids was performed by ionic chromatography after bubbling the gas through water.

Water content determination was performed by the Karl Fischer method after bubbling the gas through n-propanol.

It was determined that the purified gas contained 96 ppm of acids and 0.34% of water, relative to the total weight of the gas.

EXAMPLE 2

An apparatus of the type shown in FIG. 2, including the various units of the apparatus of Example 1, and in addition an absorption column with six perforated trays, was employed for purifying the same mixture as that in Example 1.

The operating parameters of Example 1 were retained, except that the condenser cooled the gases from the top of the cooling column to 4° C.

The gaseous fraction recovered on leaving the condenser was introduced at the bottom of the absorption column at a flow rate of 16.2 kg/h. A stream of water circulated in this absorption column, and was introduced at 4° C. above the first tray of the column, at a flow rate of 0.2 kg/h.

As in Example 1, it was determined that the gaseous stream that left the absorption column contained 0.43% of water and less than 10 ppm of acids, relative to the total weight of the gaseous stream.

What is claimed is:

1. A process for purifying acrolein present in a feed gas stream including acrolein, water, acids and inert gases, which comprises, in a first stage, fractionating the feed gas stream into a gaseous effluent and a liquid stream in a cooling column, said cooling column operating such that the temperature of the liquid stream at the bottom of said cooling column is lower than or equal to the condensation temperature of the feed gas stream, the difference in temperature being less than 20° C., and, in a second stage, condensing the gaseous effluent at a temperature that is lower than 20° C. to give a liquid fraction and a purified gaseous fraction.

2. A process according to claim 1, wherein said feed gas stream originates from a gas-phase oxidation reaction of propylene to acrolein.

3. A process according to claim 1, wherein the temperature of the liquid stream at the bottom of the cooling column is lower than or equal to the condensation temperature of the feed gas stream, the difference in temperature not exceeding 10° C.

4. A process according to claim 1, wherein the purified gaseous fraction contains a water content less than or equal to 2% by weight and a weight content of acids less than or equal to 100 ppm.

5. A process according to claim 1, wherein the feed gas stream is introduced into the cooling column at a temperature ranging from 100° to 200° C., the temperature of the gaseous effluent at the top of said column ranges from 30° to 60° C., and the temperature of the liquid stream is substantially equal to the condensation temperature of the feed gas stream.

6. A process according to claim 1, wherein said feed gas stream contains from about 10 to 15% by weight of acrolein, from about 20 to 30% by weight of water, and less than 5% by weight of acrylic acid.

7. A process according to claim 1, wherein said cooling column operates at a pressure ranging from $10^5$ to $3 \times 10^5$ Pa.

8. A process according to claim 1, wherein the feed gas stream resides in said cooling column for a time period ranging from 5 to 10 minutes.

9. A process according to claim 1, wherein a portion of the liquid stream at the bottom of the cooling column is removed, optionally cooled, and recycled as circulating liquid stream in the cooling column.

10. A process according to claim 9, wherein an acrolein polymerization inhibitor selected from hydroquinone, phenothiazine and derivatives of phenothiazine is added to said recycled liquid stream.

11. A process according to claim 9, wherein said recycled liquid stream contains less than 2% by weight of acrolein and at least 90% by weight of water.

12. A process according to claim 9, wherein the temperature of said recycled liquid stream, before circulation in the cooling column, ranges from 15° to 45° C.

13. A process according to claim 1, wherein a portion of said liquid stream at the bottom of said cooling column is stripped using a stripping gas to provide a stripped gaseous stream containing acrolein that is then introduced into said cooling column with said feed gas stream.

14. A process according to claim 13, wherein said stripping occurs by heating said liquid stream to a temperature ranging from 90° to 120° C. and introducing said heated liquid stream into a column where it is circulated countercurrentwise to said stripping gas.

15. A process according to claim 14, wherein the temperature of said stripping gas ranges from 130° to 160° C.

16. A process according to claim 1, further comprising the step of passing said purified gaseous fraction through an absorption operation by countercurrentwise circulating of said gaseous fraction with water at a mass flow rate of water, wherein the ratio of the mass flow rate of water to the mass flow rate of the gaseous fraction ranges from 0.005:1 to 0.05:1, and wherein the water temperature is lower than the temperature of said purified gaseous fraction.

17. A process according to claim 1, wherein said condensing is carried out in the presence of an acrolein polymerization inhibitor selected from hydroquinone, phenothiazine and derivatives of phenothiazine.

18. An apparatus for purifying acrolein present in a feed gas stream, which apparatus comprises a cooling column, said cooling column having a supply for the feed gas stream and a condensation unit, wherein said condensation unit is fed by gas from the top of said cooling column.

19. An apparatus according to claim 18, wherein said feed gas stream originates from a gas-phase oxidation of propylene to acrolein.

20. An apparatus according to claim 18, wherein the liquid from the bottom of said cooling column is circulated to a point at the upper part of said cooling column and optionally cooled before re-entering the cooling column.

21. An apparatus according to claim 18, wherein the level of liquid at the bottom of said cooling column is controlled by a draw-off valve.

22. An apparatus, according to claim 18, further comprising a stripping column, wherein said stripping column is fed by the liquid from the bottom of said cooling column and circulates the means for the gas from the top of said stripping column to the supply for the feed gas stream or to the lower part of said cooling.

23. An apparatus according to claim 22, which further comprises a preheater installed upstream of said stripping column to raise the temperature of the liquid to be stripped.

24. An apparatus according to claim 22, further comprising a heat exchanger installed at an intermediate location upstream of said stripping column.

25. An apparatus according to claim 18, further comprising a liquid/gas absorption column, wherein said liquid/gas absorption column is fed in its lower part by gas leaving said condensation unit and in its upper part by a water delivery conduit.

26. An apparatus according to claim 18, wherein liquid condensed in said condensation unit is introduced into the upper part of said cooling column at a point of said cooling column close to a point at the upper part of said cooling column.

27. An apparatus according to claim 18, wherein said condensation unit is placed in the upper part of a cooling column which is located inside a single column.

28. An apparatus according to claim 18, wherein said condensation unit is placed in the upper part of a cooling column and an absorption unit is placed above said condensation unit inside a single column.

* * * * *

UNITED STATES PATENT AND TRADEMARK OFFICE
CERTIFICATE OF CORRECTION

PATENT NO. : 5,770,021
DATED : June 23, 1998
INVENTOR(S) : HEGO et al.

It is certified that error appears in the above-identified patent and that said Letters Patent is hereby corrected as shown below:

Claim 22, column 12, line 6, after "cooling", insert --column--.

Signed and Sealed this

Twenty-fifth Day of May, 1999

Attest:

Q. TODD DICKINSON

*Attesting Officer*    Acting Commissioner of Patents and Trademarks